United States Patent
Kobayashi et al.

(10) Patent No.: US 8,597,417 B2
(45) Date of Patent: Dec. 3, 2013

(54) BLOOD RESERVOIR

(75) Inventors: Susumu Kobayashi, Osaka (JP);
Takashi Arai, Osaka (JP); Yuji Kuwahara, Osaka (JP)

(73) Assignee: Nipro Corporation, Osaka (JP)

( * ) Notice: Subject to any disclaimer, the term of this patent is extended or adjusted under 35 U.S.C. 154(b) by 208 days.

(21) Appl. No.: 13/123,460

(22) PCT Filed: Oct. 2, 2009

(86) PCT No.: PCT/JP2009/067253
§ 371 (c)(1),
(2), (4) Date: Jul. 1, 2011

(87) PCT Pub. No.: WO2010/041604
PCT Pub. Date: Apr. 15, 2010

(65) Prior Publication Data
US 2011/0247502 A1 Oct. 13, 2011

(30) Foreign Application Priority Data

Oct. 9, 2008 (JP) ................................ 2008-263100
Oct. 9, 2008 (JP) ................................ 2008-263101

(51) Int. Cl.
*B01D 19/00* (2006.01)

(52) U.S. Cl.
USPC ................ 96/219; 96/179; 95/243; 95/259; 95/242

(58) Field of Classification Search
USPC ................ 96/219, 179; 95/243, 259, 242
See application file for complete search history.

(56) References Cited

U.S. PATENT DOCUMENTS

| 4,898,572 A | 2/1990 | Surugue nee Lasnier et al. |
| 5,411,705 A * | 5/1995 | Thor et al. ................. 422/45 |
| 5,800,721 A * | 9/1998 | McBride ................... 210/806 |
| 5,849,186 A * | 12/1998 | Raneri et al. ............. 210/315 |

FOREIGN PATENT DOCUMENTS

| JP | 62-27964 | * | 2/1987 |
| JP | 5-317420 A | | 12/1993 |
| JP | 06-343694 A | | 12/1994 |
| JP | 2003-111835 A | | 4/2003 |
| JP | 2008-194386 | * | 8/2008 |
| JP | 2008-194386 A | | 8/2008 |

* cited by examiner

*Primary Examiner* — Duane Smith
*Assistant Examiner* — Douglas Theisen
(74) *Attorney, Agent, or Firm* — Sughrue Mion, PLLC

(57) ABSTRACT

A blood reservoir (1) including a venous blood filter (40) and a cardiotomy filter (5). The cardiotomy blood filter includes a first cardiotomy blood filter member (51) and a second cardiotomy blood filter member (52). The filter member (52) is equipped with a first filter portion (52a) and a second filter portion (52b). The first filter portion (52a) forms the wall portion and the second filter portion (52b) forms the bottom portion. Specifications of the first filter portion (52a) and the second filter portion (52b) are different. A guide member (60) of the blood storage tank (1) is made of a foam material. The blood from which bubbles have been removed is guided while permeating the guide member (60). Consequently, the guide member (60) can lead the blood from which bubbles are removed to a predetermined position at a suitable liquid impact speed.

11 Claims, 7 Drawing Sheets

| Angle of Inclination $\alpha$ | Density D ($g/cm^3$) |
|---|---|
| $70 \leqq \alpha$ | $0.02 < D \leqq 0.05$ |
| $65° \leqq \alpha < 70°$ | $0.05 < D \leqq 0.20$ |
| $\alpha < 65°$ | $0.20 < D \leqq 0.40$ |

BLOOD RESERVOIR

TECHNICAL FIELD

The present invention relates a blood reservoir that has a filter member.

BACKGROUND ART

An artificial heart lung apparatus is used during conventional cardiac surgery. The artificial heart lung apparatus is mainly configured from a blood reservoir, a blood pump, a heat exchanger, a blood circuit, an oxygenator, and the like. In this type of artificial heart lung apparatus, firstly blood (venous blood) that was removed from veins of the patient and blood (cardiotomy blood) that is withdrawn from the field of operation are sent to a blood reservoir, and temporarily stored in the blood reservoir. Furthermore, blood is sent to the heat exchanger by the blood pump, and the heat exchanger adjusts the blood temperature. In the oxygenator, gas exchange (carbon dioxide removal and oxygen addition) is performed on the temperature-adjusted blood. Finally, the blood is returned to the body of the patient as arterial blood.

This type of artificial heart lung apparatus provides a temporary substitution for the function of the heart and lungs during cardiac surgery. In the artificial heart lung apparatus, before returning the blood to the patient, foreign material or bubbles that have become mixed in the blood during surgery must be removed. For example, JP-H5-317420 (called "Patent Document 1" hereinafter) discloses a blood reservoir (blood reservoir including a cardiotomy reservoir) that removes simultaneously bubbles and foreign matter such as bone fragments, soft-tissue fragments, or the like from blood.

SUMMARY

The conventional blood reservoir, for example, is provided with a mesh-shaped filter for removal of bubbles and foreign matter. The mesh-shaped filter may be a woven fabric, a non-woven fabric or the like (refer to Patent Document 1). For example, when a non-woven fabric is used as a filter, stable blood processing is enabled since the non-woven fabric does not tend to clog. On the other hand, when removing air bubbles of at least a specific size and over, since a non-woven fabric has low liquid permeable characteristics in comparison to a mesh fabric, blood tends to accumulate, and the permeate rate decelerates. In other words, the time until the amount of blood in the blood reservoir appears as a change of the liquid surface is increased. Therefore, when using a conventional blood reservoir, there is the problem that a clinical engineer, nurse, doctor, or the like who manages the blood reservoir has difficulty in accurately comprehending the amount of blood that has left the patient, that is to say, the blood storage amount (Problem 1).

A portion of the bottom portion of a conventional blood reservoir has a protruding portion that projects outwardly. A venous blood filter for removing bubbles from the venous blood is disposed above the protruding portion. Furthermore, a cardiotomy blood filter is disposed at a position adjacent to the venous blood filter, that is to say, inclining above the protruding portion. When foreign matter or bubbles are removed from cardiotomy blood by the cardiotomy blood filter, in case that the storage blood amount is low, the cardiotomy blood falls to the bottom face (non-protruding portion) that is adjacent to the protruding portion of the blood reservoir. Thus, the cardiotomy blood flows in contact with the bottom face from the non-protruding portion of the blood reservoir towards the protruding portion, and is stored in an inner space of the protruding portion.

In this manner, when there is a low storage blood amount in the conventional blood reservoir, since cardiotomy blood from which foreign matter and bubbles have been removed by the cardiotomy blood filter flows into an inner portion of the protruding portion while making contact with the bottom face of the blood reservoir, there is the problem that time is required for the cardiotomy blood to reach the inner space in the protruding portion. In other words, notwithstanding the fact that foreign matter and bubbles have been already removed from the cardiotomy blood by the cardiotomy blood filter, there is the problem that time is required to reflect that cardiotomy blood as a blood storage amount. Consequently, when actually using this type of blood reservoir, the medical personnel such as a clinical engineer, nurse, doctor, or the like who manages the blood reservoir have difficulty in accurately comprehending the blood storage amount during the surgical procedure.

In order to solve the above problem, a blood reservoir has been developed in which the cardiotomy blood filter is disposed above the protruding portion. In this type of blood reservoir, since the cardiotomy blood filter is disposed above the protruding portion, when foreign matter or bubbles are removed from the cardiotomy blood by the cardiotomy blood filter, the cardiotomy blood drops into an inner portion of the protruding portion of the blood reservoir. Therefore, when using this type of blood reservoir, cardiotomy blood from which foreign matter and bubbles have been removed by the cardiotomy blood filter is promptly reflected as a blood storage amount. However, when the blood storage amount is low, since there is an increase in the dropping distance from the position at which the cardiotomy blood from which foreign matter and bubbles have been removed starts to drop to the portion in which the blood is stored in an inner portion of the protruding portion, there is the problem that bubbles become mixed as a result of the drop (Problem 2).

The present invention is proposed in light of the above Problem 1, and an object of the present invention is to provide a blood reservoir that has a filter having a processing capacity that is desired by medical personnel. Furthermore, the present invention is proposed in light of Problem 2 above, and an object of the present invention is to prevent occurrence of bubbles in blood after bubble removal. In addition, a further object of the present invention is to enable accuracy comprehension of a blood storage amount by medical personnel.

A blood reservoir according to embodiment 1 stores venous blood and/or cardiotomy blood. The blood reservoir includes a housing and a filter means. The filter means is disposed in the housing. The filter means includes a filter member.

More precisely, the blood reservoir includes a housing, a venous blood filter means, and a cardiotomy blood filter means. The venous blood filter means includes a venous blood filter member. The venous blood filter member removes bubbles from the venous blood. The venous blood filter member is disposed in the housing. The cardiotomy blood filter means includes a first cardiotomy blood filter member and a second cardiotomy blood filter member. The first cardiotomy blood filter member removes foreign matter and bubbles from cardiotomy blood, and is disposed in the housing. The second cardiotomy blood filter member removes foreign matter and bubbles from cardiotomy blood that has passed through the first cardiotomy blood filter member, and is disposed outside the first cardiotomy blood filter member.

In particular, this blood reservoir includes a filter member that removes foreign matter and bubbles from the blood that was removed from the patient. The filter member includes a first filter portion and a second filter portion. The first filter portion forms a wall portion and the second filter portion forms a bottom portion. The first filter portion and the second filter portion are formed with different specifications.

This type of blood reservoir is provided with a filter means, and the filter means has a filter member. As a result, a blood reservoir that responds to the requirements of medical personnel can be provided by provision of a filter member having a specification that responds to the requirements of medical personnel.

More specifically, the blood reservoir includes a cardiotomy blood filter means. This cardiotomy blood filter means includes a second cardiotomy blood filter member. Consequently, a blood reservoir that responds to the requirements of medical personnel can be provided by provision of a second filter having a specification that responds to the requirements of medical personnel.

Still more specifically, the cardiotomy blood filter means includes a first cardiotomy blood filter member. Consequently, foreign matter and bubbles having a relatively large size can be removed from cardiotomy blood flowing into the blood reservoir by the first cardiotomy blood filter member. Furthermore, when blood flows from the first cardiotomy blood filter member to the second cardiotomy blood filter member, small sized foreign matter and bubbles can be removed by the first cardiotomy blood filter member. In this manner, foreign matter can be removed from the blood that has passed through the cardiotomy blood filter means, and bubbles included in the blood that has passed through the cardiotomy blood filter means can be accurately limited to a predetermined size less or equal.

In particular, this blood reservoir includes a filter member that is composed of the first filter portion and the second filter portion to remove foreign matter and bubbles from the blood that has bled from the patient. The first filter portion forms a wall portion, and the second filter portion that is formed with a different specification from the first filter portion forms the bottom portion. Consequently, a filter member having the processing capacity that is required by medical personnel can be provided by separating the specification that responds to the requirements of medical personnel into the wall portion (first filter portion) and the bottom portion (second filter portion).

The blood reservoir includes a venous blood filter means, and the venous blood filter means includes a venous blood filter member. Consequently, a blood reservoir that enables removal of foreign matter and bubbles from cardiotomy blood and enables removal of bubbles from venous blood can be provided.

As described above, this blood reservoir is a blood reservoir that has the processing capacity required by medical personnel. In this manner, medical personnel managing the blood reservoir can more accurately comprehend the blood storage amount held in the blood reservoir.

The blood reservoir according to embodiment 2 includes the blood reservoir according to embodiment 1 in which the second filter portion is formed in a projecting shape.

In this configuration, since the second filter portion in the filter member, that is to say, the bottom portion, is formed in a projecting shape, the contact surface area with blood can be increased. In this manner, the blood processing capacity in the filter member can be improved.

The blood reservoir according to embodiment 3 includes the blood reservoir according to embodiment 1 or embodiment 2, in which the second filter portion is connected to the first filter portion to enable folding towards an inner surface of the first filter portion. When the second filter portion is folded, the second filter portion is formed in a projecting shape.

In this configuration, the filter member can be easily processed and manufactured since the second filter portion is connected with the first filter portion to enable folding towards an inner surface of the first filter portion. When the second filter portion is folded, the second filter portion can increase the contact surface area with blood. In this manner, the blood processing capacity in the filter member can be improved.

The blood reservoir according to embodiment 4 includes the blood reservoir according to any one of embodiment 1 to embodiment 3, in which the second filter portion has a specification that enables higher liquid permeable characteristics than the first filter portion.

In this configuration, the second filter portion in the filter member has higher liquid permeation characteristics than the first filter portion. As a result, when blood begins to flow into the inner portion of the filter member, the blood mainly flows through the second filter portion. When the blood processing capacity in the second filter portion is reduced by blocking or the like, the blood begins to mainly flow through the first filter portion. In this manner, when blood mainly flows through the second filter portion, high-speed removal of foreign matter and bubbles from the blood is enabled. Thereafter, when blood mainly flows through the first filter portion, although the blood processing speed of the second filter portion is reduced, stable removal of foreign matter and bubbles from the blood is enabled.

The blood reservoir according to embodiment 5 includes the blood reservoir according to embodiment 4, in which the first filter portion is formed by a non-woven fabric. Furthermore, the second filter portion is formed by a single-layer mesh fabric.

In this configuration, the first filter portion is formed from a non-woven fabric. Furthermore the second filter portion is formed from a single-layer mesh fabric (screen mesh). In this manner, when blood is mainly passing through the mesh fabric, high-speed removal of foreign matter and bubbles from the blood is enabled. Thereafter, when blood mainly flows through the non-woven fabric, although the blood processing speed of the mesh fabric is reduced, stable removal of foreign matter and bubbles from the blood is enabled.

The blood reservoir according to embodiment 6 includes the blood reservoir according to any one of embodiment 1 to embodiment 5, and is a blood reservoir that stores venous blood and/or cardiotomy blood. This blood reservoir includes a housing, a filter means, and a guide member. The housing includes a blood inflow portion and a blood outflow portion. The filter means filters blood inflowing from an inflow portion. The filter means is disposed in the housing. The guide member is disposed between the filter means and an outflow portion, and guides blood that is filtered by the filter means towards the outflow portion. The guide member is configured from a foam material.

The blood reservoir includes the guide member. The guide member is disposed between the filter means and the outflow portion, and therefore blood that has been filtered by the filter means can be accurately guided to the outflow portion at a suitable liquid impact speed. Since the guide member is configured from a foam material, blood that bubbles are removed is guided while permeating through the guide member. In this manner, the guide member can guide blood after bubble removal to a predetermined position at a suitable liquid impact speed. In other words, the guide member can prevent entry of bubbles into the blood after filtering. Furthermore, medical personnel who manage the blood reservoir can more accurately comprehend the blood storage amount stored in the blood reservoir.

The blood reservoir according to embodiment 7 includes the blood reservoir according to embodiment 6, and is a blood reservoir that stores venous blood and/or cardiotomy blood. This blood reservoir includes a housing, a venous blood filter, a cardiotomy blood filter, and a guide member. The housing includes a blood inflow portion and a blood outflow portion. The venous blood filter means includes a venous blood filter member for removal of bubbles from the venous blood. The venous blood filter means is disposed in the housing. The cardiotomy blood filter means includes a first cardiotomy blood filter member, and a second cardiotomy blood filter member. The first cardiotomy blood filter member removes foreign matter and bubbles from the cardiotomy blood, and is disposed in the housing. The second cardiotomy blood filter member removes foreign matter and bubbles from the cardiotomy blood that has passed through the first cardiotomy blood filter member, and is disposed outside the first cardiotomy blood filter member. The guide member is disposed between the cardiotomy blood filter means and the outflow portion, and guides blood filtered by the cardiotomy blood filter means towards the outflow portion.

In this configuration, the blood reservoir includes a guide member. The guide member is disposed between the cardiotomy blood filter means and the outflow portion, and ensures guiding of blood filtered by the cardiotomy blood filter means towards the outflow portion without scattering. In other words, the guide member prevents mixture of bubbles in the filtered blood. Furthermore, medical personnel who manage the blood reservoir can more accurately comprehend the blood storage amount stored in the blood reservoir.

The blood reservoir according to embodiment 8 includes the blood reservoir according to embodiment 6 or embodiment 7, in which the guide member is a plate shaped member which is compressed with respect to the thickness direction.

In this configuration, the predetermined foam material that configures the guide member is compressed with respect to a thickness direction, and therefore an elongated hole can be formed in direction that is orthogonal to the thickness direction in the guide member. In this manner, blood that is guided to permeate the guide member can be guided smoothly in a direction that is orthogonal to the thickness direction, and at the same time, bubbles do not tend to remain in the member.

The blood reservoir according to embodiment 9 includes the blood reservoir according to any one of embodiment 6 to embodiment 8, and the guide member is disposed at an angle of inclination that depends on the density of the material density.

In this configuration, the angle of inclination of the guide member is set to an angle that varies in response to the density of the material configuring the guide member. Generally, the spaces in the guide member are reduced as the density of the material configuring the guide member increases. In this manner, when the density of the material configuring the guide member increases, blood is hindered from permeating the guide member. In other words, when the density of the material configuring the guide member increases, blood does not permeate the guide member and flows on the surface of the guide member. For this reason, when the density of the material configuring the guide member increases, the speed that the blood travels over the guide member increases.

For the above reasons, for example, blood after bubble removal can be guided to a predetermined position at a suitable liquid impact speed by disposing the guide member so that the angle of inclination of the guide member is reduced as the density of the material configuring the guide member increases. In other words, entry of bubbles into the blood after bubble removal can be prevented by the guide member.

The blood reservoir according to embodiment 10 includes the blood reservoir according to embodiment 9, and the guide member is configured from a foam material that has a density in the range from 0.02 g/cm$^3$ to 0.05 g/cm$^3$, and the angle of inclination is at least 70 degrees and over.

In this configuration, when the density of the material configuring the guide member is set in the range from 0.02 g/cm$^3$ to 0.05 g/cm$^3$, and an angle of inclination is set in the range of at least 70 degrees and over, blood after bubble removal can be guided to a predetermined position at a suitable liquid impact speed. In other words, entry of bubbles into the blood after bubble removal can be prevented by the guide member.

The blood reservoir according to embodiment 11 includes the blood reservoir according to embodiment 9, and the guide member is configured from a foam material that has a density in the range from 0.05 g/cm$^3$ to 0.20 g/cm$^3$, and the angle of inclination is from 65 degrees to 70 degrees.

In this configuration, when the density of the material configuring the guide member is set in the range from 0.05 g/cm$^3$ to 0.20 g/cm$^3$, and an angle of inclination is set in the range from 65 degrees to 70 degrees, blood after bubble removal can be guided to a predetermined position at a suitable liquid impact speed. In other words, entry of bubbles into the blood after bubble removal can be prevented by the guide member.

The blood reservoir according to embodiment 12 includes the blood reservoir according to embodiment 9, and the guide member is configured from a foam material that has a density in the range from 0.20 g/cm$^3$ to 0.40 g/cm$^3$, and the angle of inclination is less than 65 degrees.

In this configuration, when the density of the material configuring the guide member is set in the range from 0.20 g/cm$^3$ to 0.40 g/cm$^3$, and an angle of inclination is set in a range less than 65 degrees, blood after bubble removal can be guided to a predetermined position at a suitable liquid impact speed. In other words, entry of bubbles into the blood after bubble removal can be prevented by the guide member.

In the blood reservoir according to the present invention, the first filter portion forms the wall portion and the second filter portion forms the bottom portion. The first filter portion and the second filter portion are formed with different specifications. As a result, a filter member having the processing capacity that is required by medical personnel can be provided by separating the specification that responds to the requirements of medical personnel with respect to the wall portion (first filter portion) and the bottom portion (second filter portion). In this manner, medical personnel managing the blood reservoir can more accurately comprehend the blood storage amount held in the blood reservoir.

The blood reservoir according to the present invention includes a guide member that is configured from a foam material. In this manner, blood from which bubbles have been removed is guided while permeating the guide member. In this manner, the guide member can guide blood after bubble removal to a predetermined position at a suitable liquid impact speed. In other words, the guide member can prevent entry of bubbles into the blood after filtering.

The blood reservoir according to the present invention includes a guide member that is disposed between the filter means and the outflow portion, and guides blood that is filtered by the filter means towards the outflow portion at a suitable liquid impact speed. In other words, the guide member can prevent entry of bubbles into the blood after filtering.

Furthermore, medical personnel managing the blood reservoir can more accurately comprehend the blood storage amount held in the blood reservoir.

DESCRIPTION OF EMBODIMENTS

In the present invention, venous blood denotes blood that has bled from a blood vessel of a patient through a cannula, and cardiotomy blood denotes blood (vented blood or suction blood) that is withdrawn from outside or inside the heart in the surgical field (the field of operation). Furthermore, foreign material in the present invention denotes a substance other than blood that has the possibility of inclusion in cardiotomy blood such as fat globule, soft-tissue fragments, bone fragments, denatured protein, platelet clump, or the like.

Figure 1:
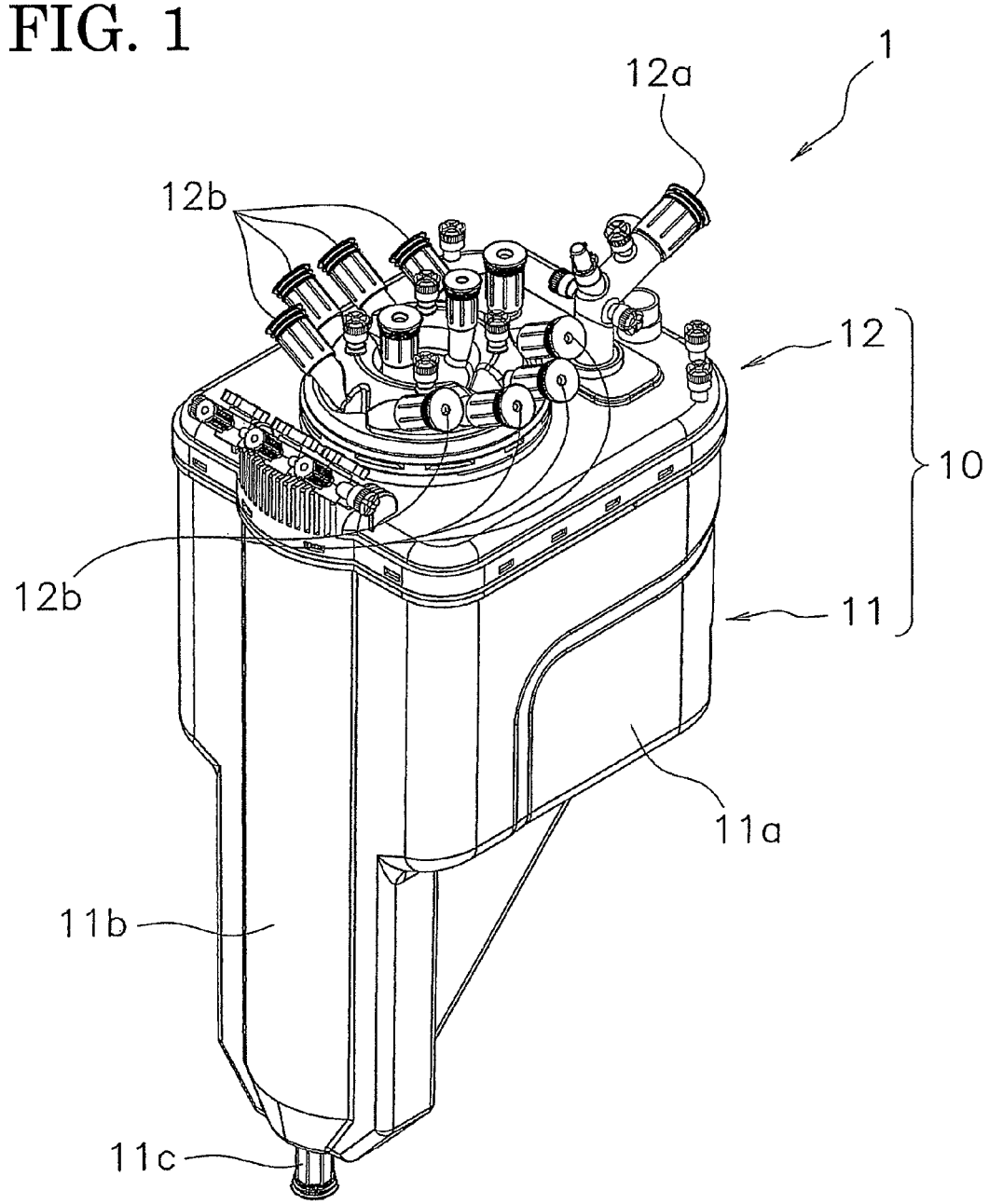
FIG. 1 is an external view of a blood reservoir according to a first embodiment of the present invention.
Figure 2:
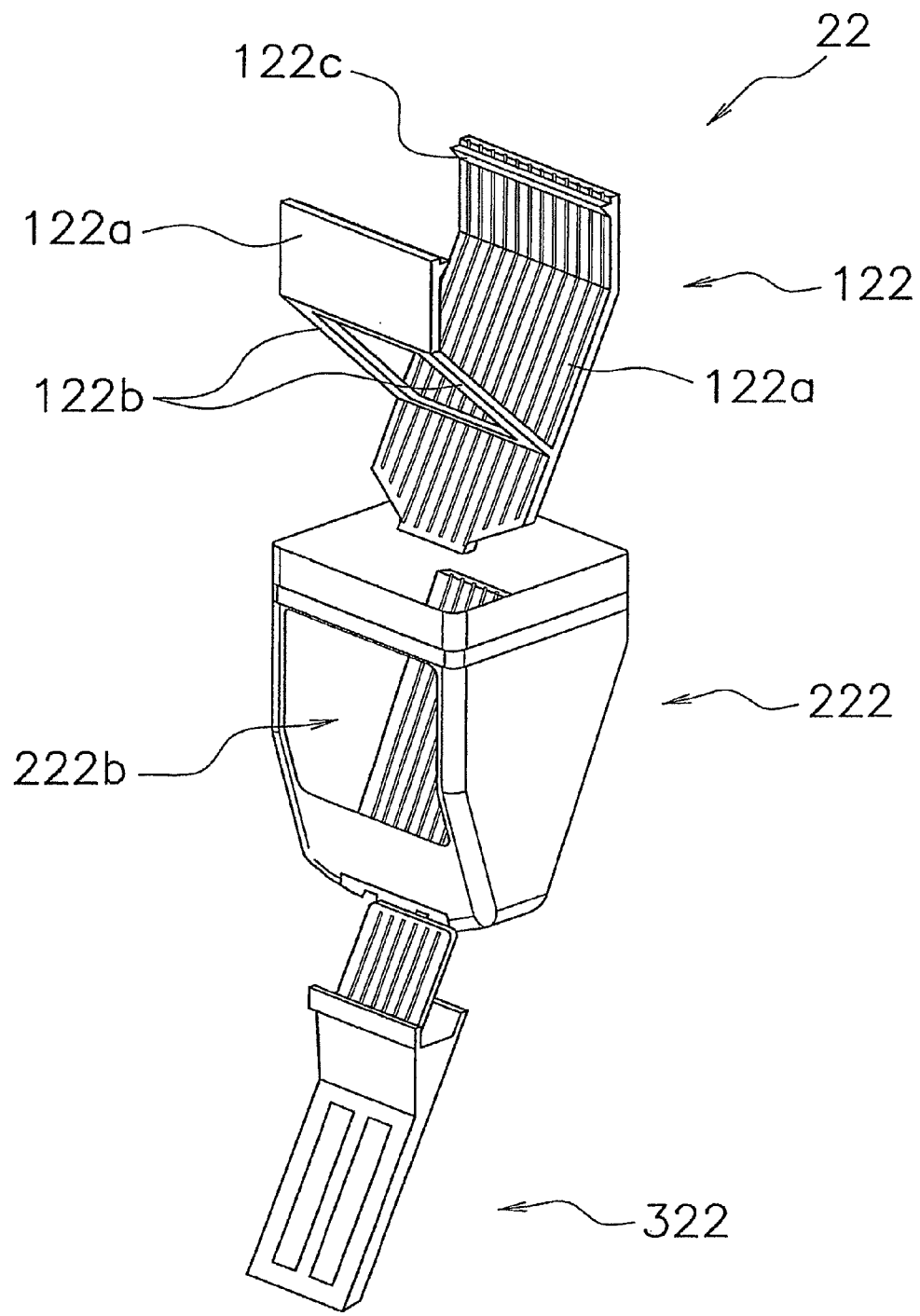
FIG. 2 is a exploded perspective view of a second support member in a filter support unit.
Figure 3:
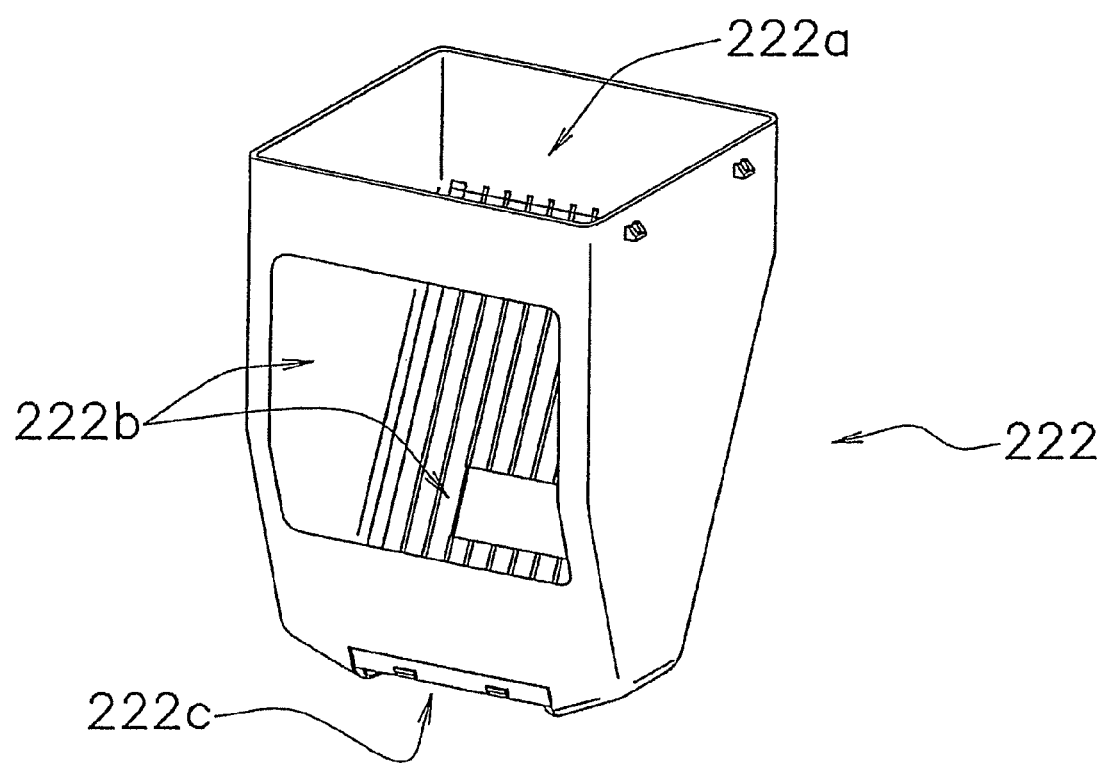
FIG. 3 is a perspective view of a filter retaining member that configures the second support member.
Figure 4:
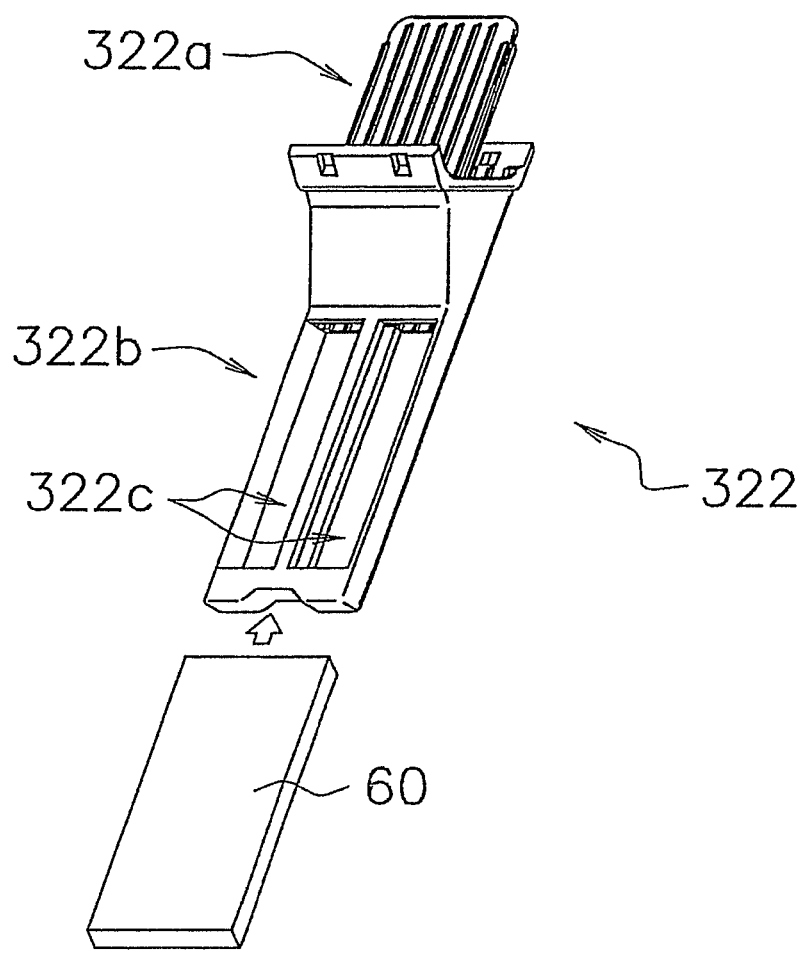
FIG. 4 is a perspective view of a bottom member that configures the second support member.
Figure 5:
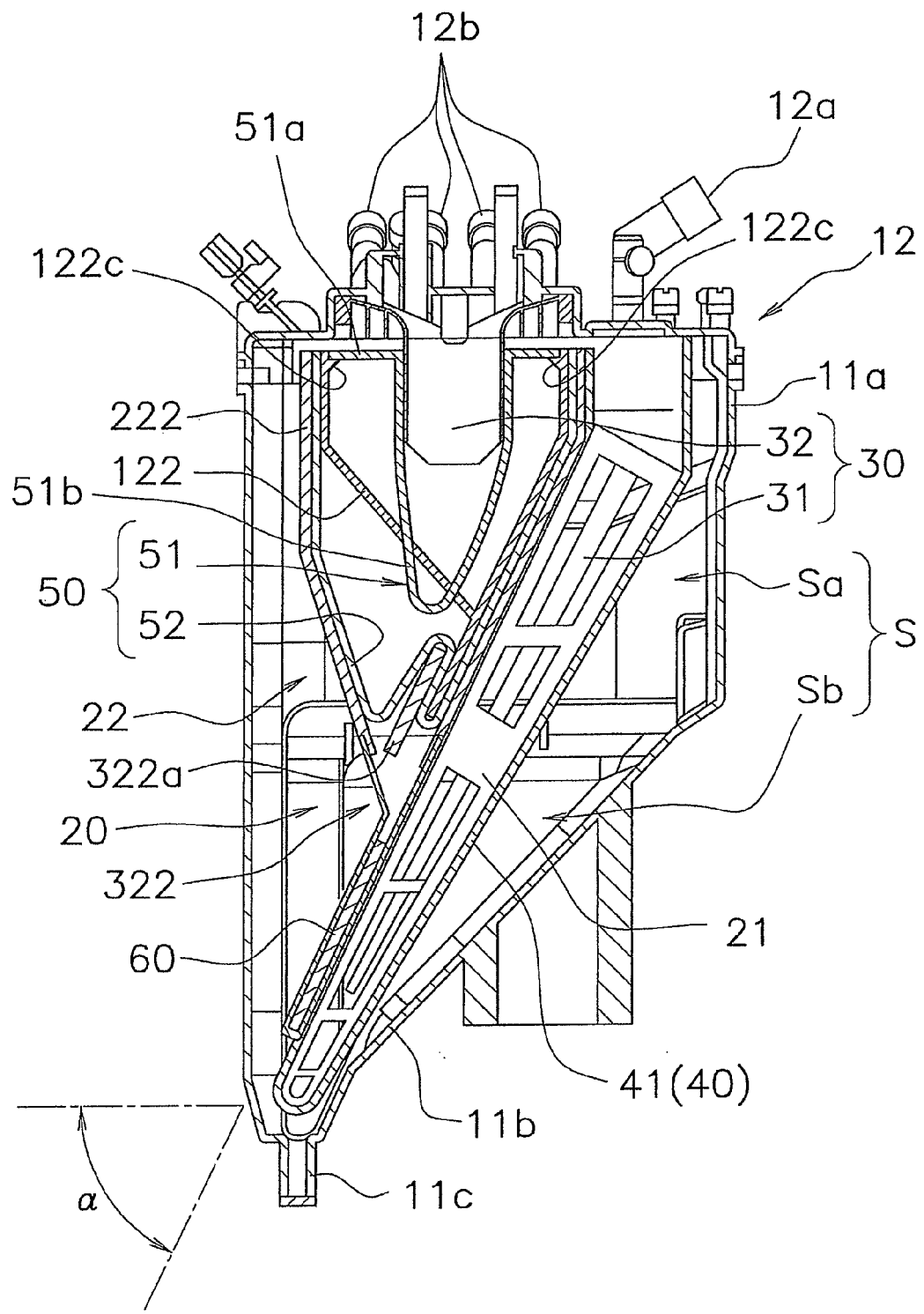
FIG. 5 is a sectional view of the blood reservoir.
Figure 6:
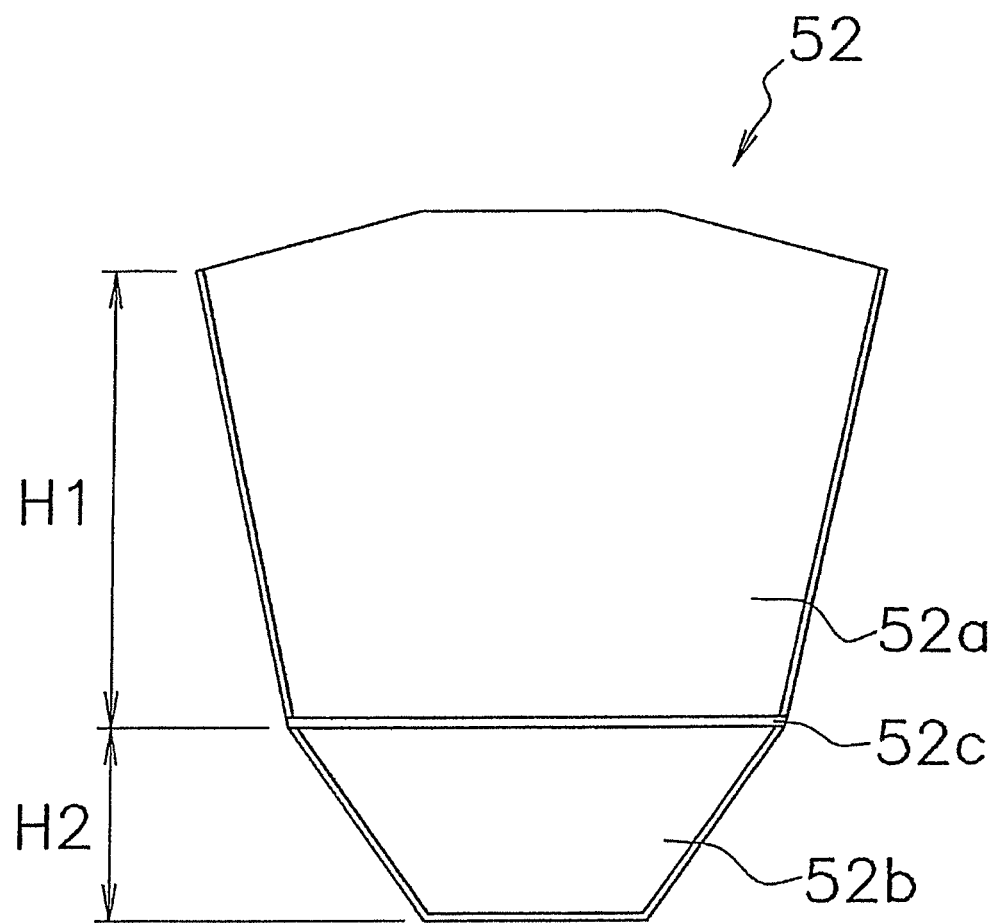
FIG. 6 is a side view of the second cardiotomy blood filter member before mounting (First View).
Figures 7, 8:
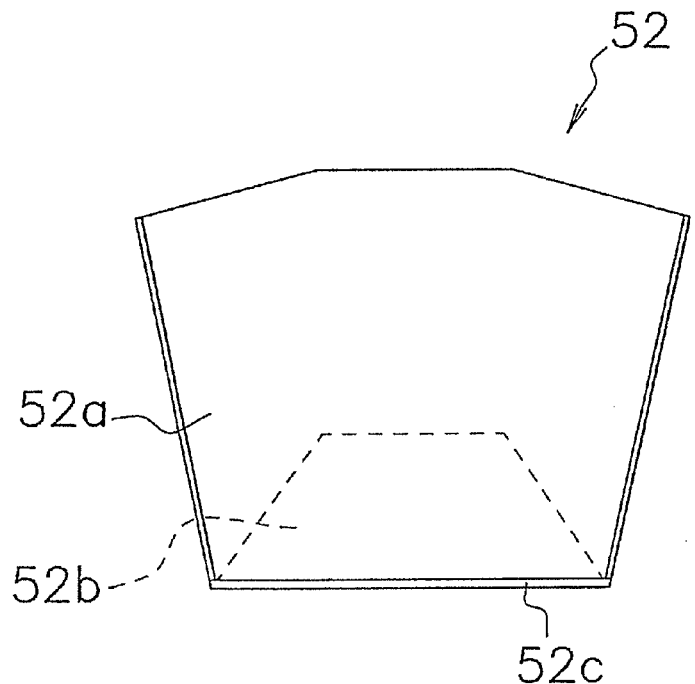
FIG. 7 is a side view of the second cardiotomy blood filter member before mounting (Second View).
FIG. 8 is a view illustrating the relationship between the angle of inclination of the guide member and the density of the material configuring the guide member.

FIG. 1 is an external view of a blood reservoir 1 according to a first embodiment of the present invention. FIG. 2 is a partial perspective view of a second support member 22 in a filter support unit 20. FIG. 3 is a perspective view of a filter retaining member 222 that configures the second support member 22. FIG. 4 is a perspective view of a bottom member 322 that configures the second support member 22. FIG. 5 is a sectional view of the blood reservoir 1. FIG. 6 and FIG. 7 are side views of the second cardiotomy blood filter member 52 before mounting. FIG. 8 is a view illustrating the relationship between the angle of inclination of the guide member and the density of the material configuring the guide member 60.

The blood reservoir 1 includes a housing 10, a filter support unit 20, a blood guiding pipe 30, a venous blood filter means 40, a cardiotomy blood filter means 50, and a guide member 60.

As shown in FIG. 1, the housing 10 includes a housing main body 11 and a cover 12. As shown in FIG. 5, a storage space S that stores blood is formed in the housing 10. The storage space S is a space inside the housing 10 that is formed by mounting the cover 12 onto the housing main body 11.

The housing main body 11 forms a box shape in which a portion has an opened configuration. The opening in the housing main body 11 is formed substantially in an oval shape, or substantially in a quadrilateral shape. As shown FIG. 1 and FIG. 5, the housing main body 11 includes a box portion 11a and a protruding portion 11b. The box portion 11a forms the storage space S on the blood inflow side, that is to say, forms an upper storage space Sa. The protruding portion 11b forms the storage space S on the blood outflow side, that is to say, forms a lower storage space Sb. The protruding portion 11b is a portion of the bottom portion of the box portion 11a that projects outwardly, and is integrally formed with the box portion 11a. A pipe-shaped blood outflow port 11c communicating from the storage space S to the outside is provided on the bottom portion of the protruding portion 11b. For example the blood outflow port 11c is connected to a tube of the blood line in the external blood recirculation path.

As used herein, one side face of the box portion 11a and one face of the protruding portion 11b are formed on the same surface. A scale (not shown) is provided on the above surface to confirm the blood storage amount. The bottom portion of the box portion 11a and the bottom portion of the protruding portion 11b face the opening of the housing main body 11.

As shown in FIG. 1 and FIG. 5, the cover 12 is fitted and mounted on the housing main body 11 to cover the opening of the housing main body 11. A first blood input port 12a and a second blood inflow port 12b are provided in the cover 12. The first blood input port 12a for example is connected to a tube of a blood extraction line for venous blood in the external blood recirculation path. The second blood input port 12b for example is connected to a tube of the cardiotomy blood line in the external blood recirculation path. The first blood input port 12a and the second blood inflow port 12b communicate from an external portion to the storage space S, for example, the upper storage space Sa when the cover 12 is mounted on the housing main body 11.

An air bleed port (not shown) allowing entry and exit of air depending on fluctuation in the amount of blood in the blood reservoir 1 is provided in the cover 12. Air after defoaming or air after foam breaking is discharged to the outside from the air bleed port.

The constituent material used in the housing main body 11 and the cover 12 is for example polycarbonate, acrylic resin, polystyrene, polyvinyl chloride, or the like. The housing main body 11 formed from such a material is preferably substantially transparent in order to enable visual confirmation of the blood storage amount stored in an inner portion of the blood reservoir 1, and the state of the blood in the inner portion.

The filter support unit 20 supports the venous blood filter means 40 and the cardiotomy blood filter means 50, and is mounted on the housing 10, for example, on the cover 12. As shown in FIG. 2 to FIG. 5, the filter support unit 20 is configured from a first support member 21 and a second support member 22. The first support member 21 supports the venous blood filter means 40, for example, the venous blood filter member 41 as described hereafter. The first support member 21 has a frame structure, and is mounted onto the inner surface of the cover 12.

As shown in FIG. 2 to FIG. 5, the second support member 22 supports the cardiotomy blood filter means 50, for example, the first cardiotomy blood filter member 51 and the second cardiotomy blood filter member 52 as described hereafter. The second support member 22 is mounted onto the inner surface of the cover 12. More specifically, the second support member 22 includes a frame 122, a filter retaining member 222 that retains the second cardiotomy blood filter member 52 with the frame 122, and a bottom member 322 that supports the bottom portion of the second cardiotomy blood filter member 52.

The frame 122 is mounted onto the inner surface of the cover 12. The frame 122 includes two opposed plate portions 122a, a connecting member 122b connecting the two plate portions 122a, and a mesh portion 122c formed on an inner face of each plate portion 122a. The second support member 22 is mounted on the inner surface of the cover 12 in the two plate portions 122a. The second cardiotomy blood filter member 52 covers the plate portion 122a and the connecting member 122b. The second cardiotomy blood filter member 52 engages the plate portion 122a and is mounted onto the plate portion 122a.

The filter retaining member 222 is mounted on the inner surface of the cover 12. The filter retaining member 222 is formed in a box shape along the outer shape of the frame 122. An opening is formed on the upper portion, the central portion and the lower portion of the filter retaining member 222. The upper portion of the opening 222a is a portion for inserting the frame 122. The central opening 222b is a through hole. The through hole is a passage of blood that has passed through a first filter portion 52a of the second cardiotomy blood filter member 52, for example, a non-woven fabric. The lower opening 222c is a through hole. The through hole is a passage of blood that has passed through a second filter portion 52b of the second cardiotomy blood filter member 52, for example, a mesh fabric (screen mesh). The filter retaining member 222 is mounted on the cover 12 with the second cardiotomy blood filter member 52 covered by the frame 122.

The bottom member 322 is mounted on the filter retaining member 222. More specifically, the bottom member 322 is mounted on the opening 222c formed in the filter retaining member 222. The bottom member 322 is formed to enable passage of cardiotomy blood into an inner portion in a supported configuration. In the supported configuration, the bottom member 322 supports the bottom portion (the second filter portion 52b described below) of the second cardiotomy blood filter member 52. The bottom member 322 is formed from a support portion 322a that supports the bottom portion of the second cardiotomy blood filter member 52, and a passage 322b that enables passage of cardiotomy blood from the cardiotomy blood filter means 50. The support portion 322a is formed in a plate shape, and is placed in abutment with the bottom portion of the second cardiotomy blood filter member 52 to thereby support the bottom portion of the second cardiotomy blood filter member 52.

The passage 322b is formed as a rectangular tube. In other words, the passage 322b is formed as a hollow beak shape. The opening 322c is provided on the opposed side face on the passage 322b. In this manner, cardiotomy blood that passes through the passage 322b flows out from the opening 322c in addition to the distal tip of the passage 322b.

Furthermore, when the bottom member 322 is mounted on the filter retaining member 222, the passage 322b is set to a predetermined angle of inclination α with reference to the horizontal plane (refer to FIG. 5). More specifically, the bottom member 322 is mounted on the filter retaining member 222 so that the angle of inclination α of the passage 322b relative to the horizontal plane is approximately 65 degrees.

Furthermore, when the bottom member 322 is mounted on the filter retaining member 222, the distal tip of the passage 322b of the bottom member 322 is disposed on an inner portion of the protruding portion 11b. In this manner, cardiotomy blood after filtering is guided from the upper portion of the protruding portion 11b into an inner portion of the protruding portion 11b.

The statement "a inner surface of the cover 12" as used herein means the surface opposite the side on which the first blood input port 12a and the second blood input port 12b are mounted on the cover 12. Furthermore, the statement "the top surface of the cover 12" as used herein means the surface opposite the inner surface of the cover 12. In other words, "the top surface of the cover 12" means the surface on the side on which the first blood input port 12a and the second blood input port 12b are mounted on the cover 12.

The blood guiding pipe 30 includes a venous blood guiding pipe 31 for guiding venous blood from the first blood input port 12a into an inner potion the housing 10, and a cardiotomy blood guiding pipe 32 for guiding cardiotomy blood from the second blood input port 12b into the housing 10.

The venous blood guiding pipe 31 is mounted on the inner surface of the cover 12 at the position of the first blood input port 12a. The venous blood guiding pipe 31 is formed as a pipe, and is inserted into an inner portion of the frame structure of the first support member 21. When the cover 12 is mounted on the housing main body 11, one end of the venous blood guiding pipe 31 is mounted onto the inner surface of the cover 12, and the other end is positioned in an inner portion of the protruding portion 11b. In other words, when the cover 12 is mounted on the housing main body 11, the venous blood guiding pipe 31 is disposed in the housing 10 extending from the first blood input port 12a of the cover 12 in an inclined configuration towards the protruding portion 11b of the housing main body 11.

The cardiotomy blood guiding pipe 32 is mounted on the inner surface of the cover 12 at the position of the second blood input port 12b. More specifically, the cardiotomy blood guiding pipe 32 is formed as a pipe, and is mounted on the inner surface of the cover 12 at the position of the second blood input port 12b between the second support member 22 and the cover 12. When the cover 12 is mounted on the housing main body 11, one end of the cardiotomy blood guiding pipe 32 is mounted onto the inner surface of the cover 12, and the other end is located above the protruding portion 11b. In other words, when the cover 12 is mounted on the housing main body 11, the cardiotomy blood guiding pipe 32 is disposed in the second support member 22, for example, in an inner portion of the frame 122 with extending from the second blood input port 12b of the cover 12 downwards towards the protruding portion 11b of the housing main body 11.

Although an example is described herein in which the cardiotomy blood guiding pipe 32 is mounted on the inner surface of the cover 12 at the position of the second blood input port 12b, the cardiotomy blood guiding pipe 32 may be integrally formed with the inner surface of the cover 12 at the position of the second blood input port 12b.

The venous blood filter means 40 is mounted in the housing 10. The venous blood filter means 40 includes a venous blood filter member 41. The venous blood filter member 41 removes bubbles from venous blood guided from the first blood input port 12a through the venous blood guide pipe 31 into the housing 10. For this reason, it is preferred that the hole diameter of the venous blood filter member 41 is approximately 20-40 μm.

The venous blood filter member 41 is formed as a bag with a portion thereof in an opened configuration, and is disposed in the housing 10. More specifically, the venous blood filter member 41 is formed as a bag with an upper portion thereof in an opened configuration, and is mounted on an outer surface of the first support member 21 of the filter support unit 20. Still more specifically, the venous blood filter member 41 is mounted on the first support member 21 of the filter support unit 20 to enclose the frame structure of the first support member 21 of the filter support unit 20. In this manner, when the cover 12 is mounted on the housing main body 11, the venous blood filter member 41 is disposed in the housing 10 to extend from the first blood inflow port 12a of the cover 12 inclining towards the protruding portion 11b of the housing main body 11.

The cardiotomy blood filter means 50 is mounted in the housing 10. The cardiotomy blood filter means 50 includes the first cardiotomy blood filter member 51 and the second cardiotomy blood filter member 52.

The first cardiotomy blood filter member 51 removes relatively large foreign matter and bubbles from cardiotomy blood guided from the second blood inflow port 12b through the cardiotomy blood guide pipe 32 to the inner portion of the housing 10.

The first cardiotomy blood filter member 51 is formed in a hat shape with a portion thereof in an opened configuration, and is disposed in the housing 10. The first cardiotomy blood filter member 51 is mounted onto the inner surface of the cover 12. More specifically, the first cardiotomy blood filter member 51 includes a flange portion 51a and an concave portion 51b. Still more specifically, the concave portion 51b of the first cardiotomy blood filter member 51 is fitted to the cardiotomy blood guide pipe 32, and the flange portion 51a is mounted on the inner surface of the cover 12. The flange portion 51a of the first cardiotomy blood filter member 51 is supported by the second support member 22 mounted on the cover 12. More specifically, the flange portion 51a of the first cardiotomy blood filter member 51 is supported by a claw portion 122c provided on the frame 122 of the second support member 22.

Foam urethane is used in the first cardiotomy blood filter member 51. A defoaming agent, such as silicone that defoams bubbles when coming into contact with bubbles, is coated on an inner surface of the first cardiotomy blood filter member 51, for example, on the inner surface of the concave portion 51b. For that reason, when the cardiotomy blood comes into contact with the inner surface of the first filter member 51 before cardiotomy blood passing through the first cardiotomy blood filter member 51, the bubbles contained in the cardiotomy blood are burst by the defoaming agent. After the cardiotomy blood passes through the first cardiotomy blood filter member 51, bubbles of more than a predetermined size corresponding to the size of the cavities in the first cardiotomy blood filter member 51 are removed from the cardiotomy blood. Furthermore, when the cardiotomy blood passes through the first cardiotomy blood filter member 51, foreign matter is also removed from the cardiotomy blood. For example, foreign matter having a size that is larger than the cavities of the first cardiotomy blood filter member 51 is removed from the cardiotomy blood.

The second cardiotomy blood filter member 52 removes foreign matter and bubbles from cardiotomy blood that has passed through the first filter member, that is to say, from cardiotomy blood from which relatively large foreign matter and bubbles have been removed by the second cardiotomy blood filter member 52. It is preferred that the hole diameter of the second cardiotomy blood filter member 52 is approximately 20-200 μm.

The second cardiotomy blood filter member 52 is formed as a bag with a portion thereof in an opened configuration, and is disposed in the housing 10. More specifically, the second cardiotomy blood filter member 52 is formed as a bag with an upper portion thereof in an opened configuration. In addition, the second cardiotomy blood filter member 52 is mounted on the second support member 22 of the filter support unit 20 that is disposed on an outer side of the first cardiotomy blood filter member 51. For example, the second cardiotomy blood filter member 52 is covered by the plate portion 122a and the connecting member 122b, and is engaged and mounted on the plate portion 122a. In this configuration, the filter retaining member 222 is mounted on the frame 122. The bottom member 322 is mounted in the through hole 222c that is formed in the filter retaining member 222. In this manner, the second cardiotomy blood filter member 52 is supported on the filter support unit 20 with the bottom portion folded inwardly. Furthermore in this configuration, the first cardiotomy blood filter member 51 is disposed on an inner portion of the second cardiotomy blood filter member 52.

More specifically, as shown in FIG. 6 and FIG. 7, the second cardiotomy blood filter member 52 includes the first filter portion 52a and the second filter portion 52b.

The first filter portion 52a forms a wall portion in the bag-shaped second cardiotomy blood filter member 52, that is to say, an upstream wall portion on a upstream side in the direction of the inflow of blood. The first filter portion 52a is configured from a two substantially trapezoid sheet-shaped mesh members. More specifically, the first filter portion 52a is formed by press fitting or welding the two side edges (the edges excluding the upper edge and the lower edge) of the two mesh members. The first filter portion 52a is formed for example from non-woven fabric. The first filter portion 52a is mounted on the frame 122 on the edge forming the upper opening.

The statement "substantially trapezoid" as used herein means a "trapezoid having a lower edge that projects outwardly", or "a trapezoid that has a lower edge that bends outwardly".

The second filter portion 52b forms a bottom portion on a downstream side in the direction of the inflow of blood. The second filter portion 52b is configured from a two substantially trapezoid sheet-shaped mesh members. More specifically, the substantially trapezoid sheet-shaped mesh members 52b for the second filter portion are formed so that the height H2 (height of the trapezoid) of the substantially trapezoid sheet-shaped mesh members 52b for the second filter portion is smaller than the height H1 (height of the trapezoid) of the substantially trapezoid sheet-shaped mesh members 52a for the first filter portion. More specifically, the substantially trapezoid sheet-shaped mesh members 52b for the second filter portion are preferably formed so that the height H2 of the substantially trapezoid sheet-shaped mesh members 52b for the second filter portion is approximately ⅓ of the height H1 of the substantially trapezoid sheet-shaped mesh members 52a for the first filter portion.

The two side edges (the edges excluding the upper edge and the lower edge) of the two mesh members are press fitted or welded to thereby form the second filter portion 52b. The lower edge of the second filter portion 52b (the respective lower edges of the two mesh members that configure the second filter portion 52b) are press fitted or welded to the upper edge (the respective upper edges of the two mesh members that configure the first filter portion 52a) to thereby form the second cardiotomy blood filter member 52 (refer to FIG. 6). In this configuration, the second filter portion 52b is supported on the bottom member 322, and is formed into a projecting shape on an upstream side with reference to the inflow of blood (refer to FIG. 5).

When the second cardiotomy blood filter member 52 is disposed between the frame 122 and the filter retaining member 222, and the bottom member 322 is mounted onto the lower portion of the filter retaining member 222, the second filter portion 52b is folded towards an inner surface of the first filter portion 52a on the connecting member 52c (press fitted portion or welded portion) with the first filter portion 52a (refer to FIG. 5 and FIG. 7). Consequently, the second filter portion 52b is supported on the support portion 322a of the bottom member 322. Thus, the second filter portion 52b is maintained in a projecting shape on the upstream side in the direction of the inflow of blood in the housing 10. In this configuration, when cardiotomy blood passes through the second filter portion 52b, the cardiotomy blood passes through the passage 322b of the bottom member 322.

The second filter portion 52b has a different specification from the first filter portion 52a. For example, the second filter portion 52b is formed from a material that has higher liquid permeation characteristics than the first filter portion 52a. More specifically, the second filter portion 52b is formed from a mesh fabric (screen mesh).

The term "specification" as used herein includes at least any one of structure, material, property, or the like. Herein, an example of the term "specification" in relation to structure will be described.

When the cardiotomy blood passes through the second cardiotomy blood filter member 52, foreign matter that could not be removed by the first cardiotomy blood filter member 51 is removed. Furthermore, at this time, bubbles that could not be removed by the first cardiotomy blood filter member 51 are removed from the cardiotomy blood. In other words, foreign matter and bubbles of a predetermined size that corresponds to the size of the cavities (minute holes) of the second cardiotomy blood filter member 52 are removed from the cardiotomy blood. For example, foreign matter and bubbles of at least 40 microns are removed from the cardiotomy blood as a result of the cardiotomy blood passing through the second cardiotomy blood filter member 52.

As shown in FIG. 5, the guide member 60 is disposed between the cardiotomy blood filter means 50 and the blood outflow port 11c, and is a member that guides the blood that has been filtered by the cardiotomy blood filter means 50 towards the blood outflow port 11c. More specifically, as shown in FIG. 4, the guide member 60 is mounted on the second support member 22, that is to say, on the bottom member 322. Still more specifically, the guide member 60 is formed in a plate shape, and is inserted and mounted in an inner portion of the passage 322b of the bottom member 322.

The guide member 60 is configured from a foam material compressed with respect to a direction of thickness. A material is used in the guide member 60, the material has a density D that corresponds to the angle of inclination α of the bottom member 322, for example, that corresponds to the angle of inclination α of the passage 322b of the bottom member 322. For example, the guide member 60 is configured from a material that has a density D within a range of 0.12 g/cm³ to 0.16 g/cm³. In this example, the guide member 60 is configured from a material that, has a density D of 0.13 g/cm³.

Foam urethane for example is used in the guide member 60. More specifically, compressed foam urethane in which foam urethane has been compressed is used in the guide member 60. The compressed foam urethane used in this example is a foam urethane having a thickness of 2 mm that is formed by compressing a foam urethane having a thickness of 10 mm.

For example, when commercially available foam urethane having a density of 26-30 kg/m³ is compressed in the above manner, compressed foam urethane with a density of 0.13 to 0.15 g/cm³ is obtained.

Generally, the spaces in the guide member 60 are reduced in size as the density D in the material configuring the guide member 60 increases. As a result, permeation of blood into the guide member 60 is hindered as a result of an increase in the density D of the material in the guide member 60. In other words, when the density D of the material in the guide member 60 increases, blood tends to flow across the surface of the guide member 60 without permeating the guide member 60. As a result, when the density D of the material in the guide member 60 increases, the speed of flow of blood through the guide member 60 tends to increase. Due to this reason, for example, it is desirable to dispose the guide member 60 so that the angle of inclination α of the guide member 60 is reduced as the density D of the material in the guide member 60 increases.

FIG. 5 shows an example in which the density D of the material in the guide member 60 is 0.13 g/cm³. However, due to the above reasons, when the angle of inclination a of the bottom member 322 is varied, it is desirable to vary the density D of the material.

As shown in FIG. 8, when the angle of inclination α is 70 degrees and over, it is desirable to use a porous material with a density D in the range of 0.02 g/cm³ to 0.05 g/cm³. Furthermore, when the angle of inclination α is at least 65 degrees and less than 70 degrees, it is desirable to use a porous material with a density D in the range of 0.05 g/cm³ to 0.20 g/cm³. Yet furthermore, when the angle of inclination α is less than 65 degrees, it is desirable to use a porous material with a density D in the range of 0.20 g/cm³ to 0.40 g/cm³.

The blood storage features of the blood reservoir 1 will be described below.

When venous blood reaches the blood inflow port, that is to say, the first blood inflow portion 12a, connected to the tube on the blood-extraction line for venous blood in the external blood recirculation path, the venous blood is guided into the housing 10 through the venous blood guide pipe 31. Since the distal end of the venous blood guide pipe 31 (referred to above as the other end) extends into an inner portion of the protruding portion 11b of the housing 10, the venous blood is guided into proximity with the bottom portion of the venous blood filter portion member 41. In this manner, the venous blood commences to accumulate from the bottom portion upwardly in the inner portion of the venous blood filter member 41. Thus, when the venous blood passes through the venous blood filter member 41, bubbles contained in the venous blood are defoamed by the member 41. In this manner, the venous blood is filtered by the venous blood filter member 41, that is to say, by the venous blood filter means 40, and is stored in the blood reservoir 1.

When venous blood reaches the blood inflow port, that is to say, the second blood inflow portion 12b, connected to the tube on the blood-extraction line for cardiotomy blood in the external blood recirculation path, the cardiotomy blood is guided into the housing 10 through the cardiotomy blood guide pipe 32. In this manner, the cardiotomy blood commences to accumulate in the first cardiotomy blood filter member 51. Thus, when the cardiotomy blood passes through the first cardiotomy blood filter member 51, relatively large foreign matter contained in the cardiotomy blood, for example, bone fragments, soft tissue fragments, and the like, are removed by this filter member. Furthermore, when the cardiotomy blood passes through the first cardiotomy blood filter member 51, relative large bubbles contained in the cardiotomy blood are defoamed or broken by the filter member.

In this manner, cardiotomy blood passing through the first cardiotomy blood filter member 51 starts to accumulate in the second cardiotomy blood filter member 52. When the cardiotomy blood passes through the second cardiotomy blood filter member 52, foreign matter contained in the cardiotomy blood is removed by the second cardiotomy blood filter member 52. Furthermore, when the cardiotomy blood passes through the second cardiotomy blood filter member 52, bubbles contained in the cardiotomy blood are defoamed by this filter member.

More specifically, when the cardiotomy blood that has passed through the first cardiotomy blood filter member 51 commences to accumulate in the second cardiotomy blood filter member 52, firstly foreign matter and bubbles contained in the cardiotomy blood are removed by the mesh fabric (first filter portion 52a) of the second cardiotomy blood filter member 52. Then, when the blood processing capacity of the mesh fabric is reduced by blocking or the like, foreign matter and bubbles contained in the cardiotomy blood are removed by the non-woven fabric (second filter portion 52b) of the second cardiotomy blood filter member 52. In this manner, the cardiotomy blood is filtered by the first cardiotomy blood filter member 51 and the second cardiotomy blood filter member 52, that is to say, by the cardiotomy blood filter means 50.

In this manner, the blood that has been filtered by the cardiotomy blood filter means 50 is guided towards the blood outflow port 11c by the guide member 60. More specifically, the blood guided by the guide member 60 accumulates in the protruding portion 11b of the housing 10. In this manner, the cardiotomy blood is filtered by the cardiotomy blood filter means 50, and accumulated in the lower storage space Sb of the blood reservoir 1.

The characteristics of the blood reservoir 1 will be described below.

In the present embodiment, the cardiotomy blood filter means 50 includes the second cardiotomy blood filter member 52. In the second cardiotomy blood filter member 52, the bottom portion (second filter portion 52b) is formed as a projecting shape with respect to the upstream side in the direction of blood inflow. In this manner, the blood processing capacity in the filter member can be improved.

Furthermore the second cardiotomy blood filter member 52 can be easily processed and manufactured by connection to the wall portion so that the bottom portion (second filter portion 52b) in the second cardiotomy blood filter member 52 can be folded inwardly towards the wall portion (first filter portion 52a) in the second cardiotomy blood filter member 52.

In addition, the wall portion (first filter portion 52a) in the second cardiotomy blood filter member 52 is formed from a non-woven fabric. Furthermore, the bottom portion (second filter portion 52b) in the second cardiotomy blood filter member 52 is formed from mesh fabric. Consequently, when blood starts to flow into the inner portion of the second filter member, the blood mainly passes through the mesh fabric (bottom portion). Then when the blood processing capacity of the mesh fabric is reduced by blocking or the like, the blood starts to pass through the non-woven fabric (wall portion). In this manner, when the blood is mainly passing through the mesh fabric, foreign matter and bubbles can be removed from the blood at a high speed. Thereafter, when the blood is mainly passing through the non-woven fabric, although the blood processing capacity of the mesh fabric is reduced, foreign matter and bubbles can be stably removed from the blood.

In the present embodiment, the blood reservoir 1 includes the cardiotomy blood filter means 50. The cardiotomy blood filter means 50 includes the second cardiotomy blood filter member 52. Thus the blood reservoir 1 according to the present embodiment obtains the same effect as the effect of the second cardiotomy blood filter member 52. In this manner, medical personnel who manage the blood reservoir 1 can more accurately comprehend the blood storage amount accumulated in the blood reservoir 1.

Modified Example (a) In the above embodiment, although an example was described in which cardiotomy blood was filtered by the cardiotomy blood filter means 50 in the blood reservoir 1, the feature of filtering cardiotomy blood is not limited thereby, and may take any configuration. For example, the cardiotomy blood filter means 50 may be separated, and a cardiotomy reservoir may be additionally provided. The cardiotomy blood filter means 50 may be provided in such a cardiotomy reservoir. In this configuration, venous blood is filtered in the filter means (venous blood filter means 40) of the blood reservoir, and cardiotomy blood is filtered in the filter means (cardiotomy blood filter means 50) of the cardiotomy reservoir. In this manner, the same effect as the above embodiment is obtained even when blood is filtered in the blood reservoir 1 and the cardiotomy reservoir.

INDUSTRIAL APPLICABILITY

Use is possible in relation to a blood reservoir for storing venous blood and/or cardiotomy blood.

REFERENCE SIGNS LIST

1 BLOOD RESERVOIR
10 HOUSING
11c BLOOD OUTFLOW PORT
40 VENOUS BLOOD FILTER MEANS
41 VENOUS BLOOD FILTER MEMBER
50 CARDIOTOMY BLOOD FILTER MEANS
51 FIRST CARDIOTOMY BLOOD FILTER MEMBER
52 SECOND CARDIOTOMY BLOOD FILTER MEMBER
52a FIRST FILTER PORTION
52b SECOND FILTER PORTION
60 GUIDE MEMBER
α ANGLE OF INCLINATION

The invention claimed is:

1. A blood reservoir that stores one or both of venous blood and cardiotomy blood, the blood reservoir comprising a housing and a filter means, the filter means including a venous blood filter means and a cardiotomy blood filter means, the venous blood filter means disposed in the housing and including a venous blood filter member for removing bubbles from the venous blood, and the cardiotomy blood filter means including a first cardiotomy blood filter member that is disposed in the housing and that removes foreign matter and bubbles from cardiotomy blood, and a second cardiotomy blood filter member that is disposed outside the first cardiotomy blood filter member and that removes foreign matter and bubbles from cardiotomy blood that has passed through the first cardiotomy blood filter member, the second filter member including a first filter portion that forms a wall portion and a second filter portion that forms a bottom portion, and the first filter portion and the second filter portion are formed with different specifications,
wherein the first filter portion is formed by a non-woven fabric, and the second filter portion is formed by a single-layer mesh fabric.

2. The blood reservoir according to claim 1 wherein the second filter portion is formed in a projecting shape.

3. The blood reservoir according to claim 1 wherein the second filter portion is connected to the first filter portion to enable folding towards an inner surface of the first filter portion, and when the second filter portion is folded, the second filter portion is formed in a projecting shape.

4. The blood reservoir according to according to claim 1, wherein the second filter portion has a specification that has higher liquid permeable characteristics than the first filter portion.

5. The blood reservoir according to claim 1, wherein the housing includes a blood outflow portion, and the blood reservoir further includes a guide member disposed between the filter means and an outflow portion, and guiding blood that is filtered by the filter means towards the outflow portion, the guide member configured from a foam material.

6. The blood reservoir according to claim 5 comprising a venous blood filter means and a cardiotomy blood filter means, the venous blood filter means disposed in the housing and including a venous blood filter member for removal of bubbles from the venous blood, the cardiotomy blood filter means including a first cardiotomy blood filter member that is disposed in the housing and that removes foreign matter and bubbles from the cardiotomy blood, and a second cardiotomy blood filter member that is disposed outside the first cardiotomy blood filter member and that removes foreign matter and bubbles from the cardiotomy blood that has passed through the first cardiotomy blood filter member, the guide member disposed between the cardiotomy blood filter means and the outflow portion, and guiding blood filtered by the cardiotomy blood filter means towards the outflow portion.

7. The blood reservoir according to claim 5 wherein the guide member is a plate shaped member which is compressed with respect to the thickness direction.

8. The blood reservoir according to claim 5 wherein the guide member is disposed at an angle of inclination that corresponds to the density of the material.

9. The blood reservoir according to claim 8 wherein the guide member is configured from a foam material that has a density in the range from 0.02 $g/cm^3$ to 0.05 $g/cm^3$, and the angle of inclination is at least 70 degrees and over.

10. The blood reservoir according to claim 8, wherein the guide member is configured from a foam material that has a density in the range from 0.05 $g/cm^3$ to 0.20 $g/cm^3$, and the angle of inclination is from 65 degrees to 70 degrees.

11. The blood reservoir according to claim 8, wherein the guide member is configured from a foam material that has a density in the range from 0.20 $g/cm^3$ to 0.40 $g/cm^3$, and the angle of inclination is less than 65 degrees.

* * * * *